US006277401B1

(12) United States Patent
Bello et al.

(10) Patent No.: US 6,277,401 B1
(45) Date of Patent: Aug. 21, 2001

(54) DRUG DELIVERY DEVICE

(75) Inventors: Gastone P. Bello, Monmouth Beach, NJ (US); Eli W. Packman, Merion, PA (US)

(73) Assignee: U.S. Dermatologics, Inc., Lawrenceville, NJ (US)

( * ) Notice: Subject to any disclaimer, the term of this patent is extended or adjusted under 35 U.S.C. 154(b) by 0 days.

(21) Appl. No.: 09/307,051

(22) Filed: May 7, 1999

(51) Int. Cl.⁷ ............................. A61K 9/70; A61K 37/44; A61K 31/56
(52) U.S. Cl. .................... 424/449; 424/443; 424/444; 424/445; 424/446; 424/447; 424/448; 514/179; 514/282
(58) Field of Search .................... 424/443, 444, 424/445, 446, 447, 448, 449; 514/179, 282

(56) References Cited

U.S. PATENT DOCUMENTS

| | | | |
|---|---|---|---|
| 4,627,429 | 12/1986 | Tsuk .................... | 604/307 |
| 4,710,191 | 12/1987 | Kwiatek et al. ........ | 424/449 |
| 4,839,174 | 6/1989 | Baker et al. .......... | 424/447 |
| 4,849,224 * | 7/1989 | Chang et al. .......... | 424/434 |
| 4,911,916 * | 3/1990 | Cleary ................. | 424/449 |
| 4,983,395 | 1/1991 | Chang et al. .......... | 424/448 |
| 5,008,110 * | 4/1991 | Benecke et al. ........ | 424/448 |
| 5,061,258 * | 10/1991 | Martz ................. | 603/307 |
| 5,100,669 * | 3/1992 | Hyon et al. ........... | 424/426 |
| 5,264,218 | 11/1993 | Rogozinski ............ | 424/445 |
| 5,352,711 | 10/1994 | DesMarais ............. | 521/149 |
| 5,503,844 | 4/1996 | Kwiatek et al. ........ | 424/449 |
| 5,536,263 | 7/1996 | Rolf et al. ........... | 604/307 |
| 5,593,395 * | 1/1997 | Martz ................. | 603/304 |
| 5,629,014 | 5/1997 | Kwiatek et al. ........ | 424/449 |
| 5,716,621 | 2/1998 | Bello et al. .......... | 424/443 |
| 5,741,510 | 4/1998 | Rolf et al. ........... | 424/448 |
| 5,770,220 | 6/1998 | Meconi et al. ......... | 424/448 |
| 5,807,570 * | 9/1998 | Chen et al. ........... | 424/449 |
| 5,820,876 | 10/1998 | Hoffman ............... | 424/449 |
| 5,820,877 | 10/1998 | Yamaguch et al. ....... | 424/449 |
| 5,891,461 * | 4/1999 | Jona et al. ........... | 424/449 |
| 5,891,463 | 4/1999 | Bello et al. .......... | 424/449 |

FOREIGN PATENT DOCUMENTS

| | | |
|---|---|---|
| 97/06788 | 2/1997 | (WO) . |
| 98/53825 | 12/1998 | (WO) . |

* cited by examiner

Primary Examiner—Jose' G. Dees
Assistant Examiner—Frank Choi
(74) Attorney, Agent, or Firm—Dilworth & Barrese, LLP

(57) ABSTRACT

A drug delivery device includes (a) a substantially moisture vapor permeable, liquid impermeable, flexible thermoplastic backing layer, (b) a moisture vapor permeable, flexible, oleophilic thermoplastic resin foam layer, (c) a pressure sensitive adhesive layer, and (d) a drug reservoir containing at least one hydrophilic drug composition and possessing a moisture vapor permeable, but hydrophilic drug composition impermeable, barrier layer applied to one surface thereof with the drug reservoir being applied to a portion of the adhesive layer such that the barrier layer lies between the hydrophilic drug composition and the adhesive layer thereby preventing any significant migration of the drug composition from the drug reservoir into the adhesive layer.

22 Claims, 2 Drawing Sheets

DRUG DELIVERY DEVICE

BACKGROUND OF THE INVENTION

This invention relates to a drug delivery device for the topical delivery of a hydrophilic drug or drug-containing composition.

A transdermal drug delivery device, also variously referred to as a medical bandage, treatment pad, drug patch, etc., is known. See, e.g., U.S. Pat. Nos. 4,627,429; 4,710,191; 4,839,174; 4,849,224; 4,983,395; 5,264,218; 5,503,844; 5,536,263; 5,629,014; 5,716,621; 5,741,510; 5,770,220; 5,820,876 and 5,820,877. In general, a drug delivery device will include a drug depot, or reservoir, in the form of a drug-storing matrix or carrier and an adhesive for attaching or securing the device to a surface of unbroken skin.

SUMMARY OF THE INVENTION

In accordance with the present invention, a drug delivery device is provided which comprises:

a) a moisture vapor permeable, liquid impermeable flexible thermoplastic backing layer possessing upper and lower surfaces;

b) a moisture vapor permeable, flexible, oleophilic thermoplastic foam layer possessing upper and lower surfaces, the upper surface of the foam layer being nonadhesively bonded to, and substantially coextensive with, the lower surface of the backing layer;

c) a pressure sensitive adhesive layer applied to, and substantially coextensive with, the lower surface of the foam layer; and, d) a drug reservoir containing a medicinally effective amount of at least one hydrophilic drug composition and possessing a moisture vapor permeable, but hydrophilic drug composition impermeable, barrier layer applied to one surface thereof, the drug reservoir being applied to a portion of the adhesive layer such that the barrier layer lies between the hydrophilic drug composition and the adhesive layer and prevents any significant migration of such drug composition from the drug reservoir into the adhesive layer.

The foregoing drug delivery device effectively resists delamination when pulled from the skin and since its hydrophilic drug component remains separated from the adhesive component by a hydrophilic drug composition barrier layer when the drug is contained in the drug reservoir, there is little, if any, likelihood of the hydrophilic drug composition migrating into the adhesive layer and impairing its effectiveness.

BRIEF DESCRIPTION OF THE DRAWINGS

Preferred embodiments of the invention are described below with reference to the drawings, which are described as follows:

FIG. 1b is a cross-sectional view of the drug delivery device of FIG. 1a;

FIG. 2a is a schematic top cut-away view of a drug delivery device containing a protective cover instead of a release liner in accordance with the present invention; and, FIG. 2b is a cross-sectional view of the drug delivery device of FIG. 2a.

DESCRIPTION OF THE PREFERRED EMBODIMENTS

Figure 1A:
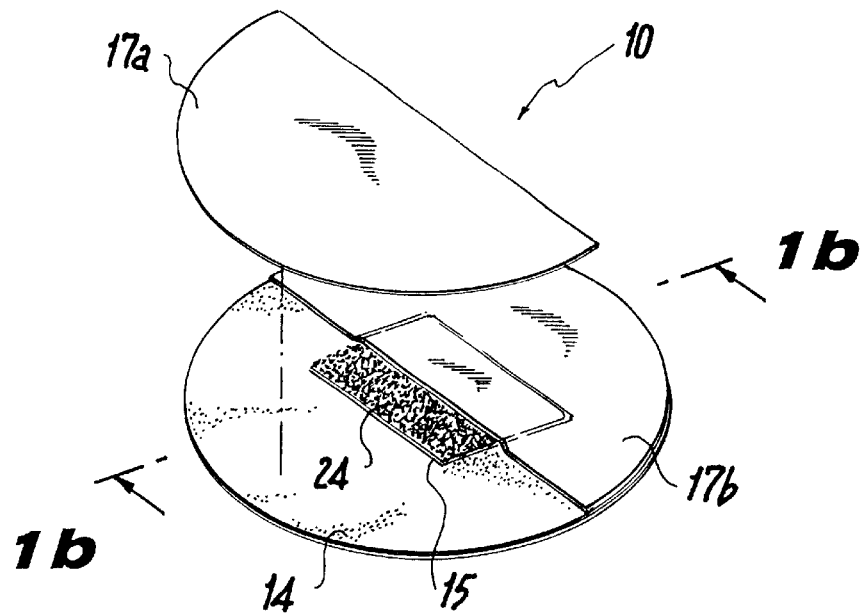
FIG. 1a is a schematic top cut-away view of a drug delivery device possessing a release liner in accordance with the present invention.
Figure 1B:
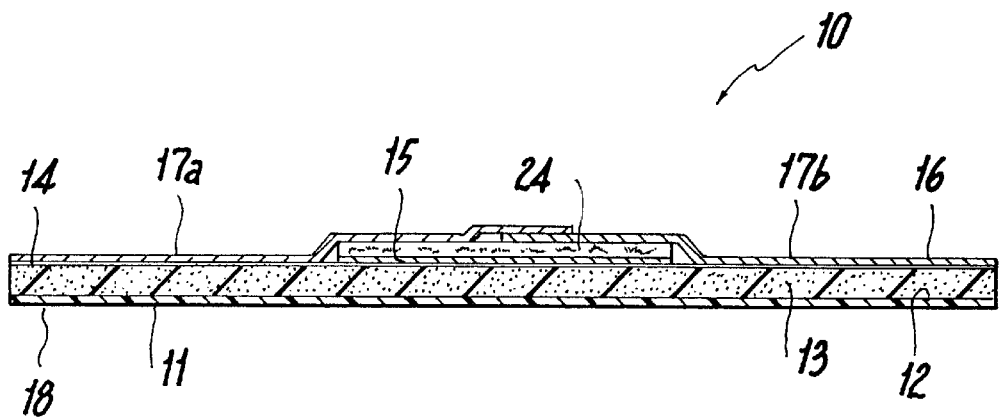

One embodiment of a drug delivery device in accordance with this invention is shown generally in FIG. 1a at 10. The drug delivery device includes a substantially moisture vapor permeable, liquid impermeable, flexible thermoplastic backing layer 11 possessing upper and lower surfaces with lower surface 18 of backing layer 11 being nonadhesively bonded to, and substantially coextensive with, upper surface 12 of moisture vapor permeable, flexible, oleophilic thermoplastic resin foam layer 13 as generally depicted in FIG. 1b. Pressure sensitive adhesive layer 14 is applied to, and substantially coextensive with, lower surface 16 of foam layer 13 for securing the drug delivery device to the skin. Drug reservoir 24 contains at least one hydrophilic drug composition and possesses a moisture vapor permeable, but hydrophilic drug composition impermeable, barrier layer 15 applied to one surface of reservoir 24. Hydrophilic drug composition barrier layer 15 is applied to at least a portion of adhesive layer 14 and separates the hydrophilic drug composition from pressure sensitive adhesive 14 thereby preventing or inhibiting any significant migration of the hydrophilic drug composition into adhesive layer 14 when the drug composition is contained in drug reservoir 24. Release liners 17a and 17b seal and protect the adhesive layer 14 and drug reservoir 24 during the residency of drug delivery device 10 within its package with release liner 17a overlapping release liner 17b.

The minimum strength of the bond between backing layer 11 and foam layer 13 must be sufficient to prevent or inhibit separation, i.e., delamination, of the backing layer from the foam layer under the sort of flexing and/or stretching forces that may be encountered during the useful life of the applied device. In general, bond strengths of at least about 2 newtons (N), preferably at least about 3 N and more preferably at least about 5 N will generally provide satisfactory results in this regard. However, for the bond between layers 11 and 13 to be achieved, it is necessary that the bond itself not result in a significant reduction in the moisture vapor transmission rate (MVTR) of the assembled layers. While known and conventional contact adhesives can readily provide backing layer-to-foam layer bond strengths of 2 N and greater, they may be disadvantageous in reducing the MVTR of the assembled layers to an unacceptable degree, e.g., a reduction of up to 25 percent in MTVR for the assembled layers employing an adhesive bonding technique versus a nonadhesive bonding technique. Accordingly, it is preferred herein to employ a nonadhesive bonding technique, e.g., one employing heat such as flame lamination that is capable of producing the desired bond strengths but without significantly reducing the MVTR of the composite formed from layers 11 and 13.

In general, the MVTR of the backing layer-foam layer subassembly will be at least about 500, preferably at least about 1000 and more preferably at least about 1200, g/m$^2$/24 h at 100% r.h. and 32° C. as measured by ASTM F1249-90.

Whatever the bond strength between backing layer 11 and foam layer 13, the contact adhesive must impart a peel strength to the drug delivery device, i.e., the amount of force required to peel the spent drug delivery device from the skin, which is less, preferably at least about 20 percent less and more preferably at least about 40 percent less, than such bond strength in order to prevent or minimize the separation of the backing layer from the foam layer when the spent drug delivery device is peeled from the skin.

Backing layer 11 can be any thermoplastic film possessing an MVTR of one of the aforestated values. Preferably, the backing layer can be a polyurethane film possessing an average thickness of from about 0.5 to about 3.5 mils and preferably from about 1.0 to about 1.5 mils and a tensile strength of at least about 2500 psi and preferably at least about 3500 psi.

Foam layer 13 in its as-manufactured state is a moisture vapor permeable, flexible, oleophilic foam that imparts flexural strength to the device since backing layer 11 is in the form of a relatively thin film thereby preventing, for example, curl-up of backing layer 11 when the device is removed from the package and/or release liners 17a and 17b are removed from adhesive layer 14. Useful foams generally possess a density of from about 0.8 to about 8.0 and preferably from about 1.2 to about 4.8 lb/ft, a number of pores per inch of from about 30 to about 120 and preferably from about 60 to about 90, and can be fully or partially reticulated or nonreticulated. The average thickness of the foam layer can vary from about 20 to about 100 mils and for many applications is preferably from about 30 to about 60 mils. Suitable foams that can be employed herein include the untreated oleophilic (i.e, hydrophobic) open cell polyurethane foams disclosed in U.S. Pat. No. 5,352,711, the contents of which are incorporated by reference herein. It is particularly advantageous to employ an oleophilic polyurethane foam over a hydrophilic polyurethane foam because when bonding a hydrophilic foam to the backing layer by way of, e,g., flame lamination or flame bonding, the heat utilized in the bonding technique would degrade the hydrophilic foam to such an extent that the backing layer-hydrophilic foam layer subassembly would be commercially unacceptable.

In general, lower surface 18 of backing layer 11 is bonded to upper surface 12 of foam layer 13 employing a suitable bonding technique, preferably, a flame lamination procedure for the reason stated above. Flame lamination, or flame bonding, the details of which are well known, involves the superficial softening or melting of upper surface 12 of foam layer 13 and while surface 12 is in this state, the application of lower surface 18 of backing layer 11 thereto. Conditions of the flame lamination operation include the temperature of the flame, the proximity of surface 12 of the foam to the flame and the duration of exposure of this surface to the flame. The conditions that are employed for a particular flame lamination operation will depend on the properties of the foam and backing layers, the bond strength desired and similar factors of which those skilled in the art are aware. For the preferred polyurethane backing film and polyurethane foam components, a flame temperature of from about 1800 to about 2200° C., a distance from the flame to the upper surface of the foam of up to about 3 cm and an exposure time of such surface of from about 25 to about 40 milliseconds will usually provide the desired minimum bond strengths or better.

In another type of nonadhesive bonding procedure, vacuum lamination, a vacuum is applied to the lower surface of the foam layer and a molten thermoplastic layer intended to provide the backing layer is cast upon the upper surface of the foam layer. The vacuum partially draws the cast layer of molten resin into the structure of the foam so that when the resin cools and solidifies, it provides the backing layer securely bonded to the foam layer.

Pressure sensitive adhesive layer 14 can be selected from any of the known and conventional medical grade adhesives, e.g., those based on polyacrylic, polyvinylether, or polyurethane resins. It is an essential requirement that the amount of adhesive 14 applied to lower surface 16 of foam layer 13 be sufficient to achieve an acceptable level of adhesion of drug delivery device 10 to the skin but, as previously stated, with a resulting peel strength that is sufficiently below the bond strength between the backing and foam layers. The amount of adhesive that will satisfy these criteria can be readily determined by simple and routine testing. Ordinarily, a medical grade polyacrylic adhesive such as Durotak® (National Starch & Chemical Company, Bridgewater, N.J.) or Gelva® (Monsanto Inc., St. Louis, Mo.) applied to a thickness of from about 1 to about 3.5 mils and preferably from about 2.0 to about 2.5 mils (depending, of course, on the thickness of the foam layer), or applied at a rate of from about 25 to about 100 $g/cm^2$ and preferably from about 50 to about 65 $g/cm^2$, will meet these requirements reasonably well.

Drug reservoir 24 can be formed from any conventional material known to one skilled in the art. Useful materials include polyurethane foam, woven or nonwoven cellulose or other natural synthetic or nonsynthetic material and the like. Generally, a large variety of hydrophilic drug compositions can be incorporated into drug reservoir 24 of drug delivery device 10 by, e.g., applying the drug in a fluid or semi-fluid state so that the composition spreads out somewhat from its initial application point to reservoir 24. However, after reaching the maximum extent of its spread and hardening, the drug composition will be lying in reservoir 24 and separated from adhesive layer 14 by barrier layer 15. The expression "hydrophilic drug" is used herein in its broadest sense as referring to any drug or drug-containing composition that can be formulated with a polar material, e.g., water, alcohols such as methanol, ethanol, propanol, isopropanol, butanol, isobutanol, etc. and the like. The drug or drug-containing composition that can be formulated with the polar material(s) can be any substance or composition possessing therapeutically or medicinally beneficial activity and includes prescription and nonprescription pharmaceuticals, medicinals, medicaments, active ingredients of cosmetic and personal care preparations, and the like.

Specific drugs that can be incorporated into hydrophilic drug composition include topically delivered local anesthetics such as benzocaine, procaine hydrochloride, tetracaine, tetracaine hydrochloride, dibucaine, lidocaine, lidocaine hydrochloride, bupivicaine, dyclonin, etidocaine, mepivicaine, butamen picrate, dimethisoquin hydrochloride, cyclomethylcaine sulfate, and the like; analgesics and anti-inflammatory agents such as buprenorphin, butophanol tartrate, acetaminophen, fentanyl, mefenamic acid, flutenamic acid, diclofenac, oxyphenbutazone, phenybutazone, ibuprofen, flurbiprofen, naproxen, menthol, methyl salicylate, phenol, salicylic acid, benzyl alcohol, camphor, camphorated metacresol, juniper tar, resorcinol, allyl isothiocyanate, capsaicin, and the like; corticosteroids such as alclometasone dipropionate, amcinocide, hydrocortisone, betamethasone dipropionate, betamethasone valerate, desoximetasone, clobetasol propionate, flurandrenolide, halcinonide, halobetasol, estradiol, testosterone, progesterone, fluticasone, clobetasol, dexamethasone, dexonide, fluocinolone acetonide, flucinonide, medroxyprogesterone, mometasone furoate, triamcinolone, and the like; antibiotics such as bacitracin, bacitracin zinc, chlortetracycline hydrochloride, chlorhexadine gluconate, clindamycin, cliquinol, neomycin sulfate, polymyxin B sulfate, erythromycin, gentamicin, sulfathiazole, sulfacetamide, sulfabenzamide, oxytetracycline hydrochloride, tetracycline, and the like; antimicrobial agents such as benzalkonium chloride, chlorhexidine gluconate, hexachlorophene, mafenide acetate, nitrofurazone, nystatin, acetosulfamine, clortrimazole, povidone-iodine, and the like; antifungal agents such as amphotericin B, butoconazole, cetylpyridinium chloride, chlorxylenol, cyclopirox olamine, clioquinol, clotrimazole, sulconazole nitrate, nystatin, oxyconazole, econazole nitrate, ketoconazole, miconazole nitrate, naftifine hydrochloride, pentamycin, pyrrolinitrin, terbinafine, triacetin, and the like; debriding agents such as deoxyribonuclease, collagenolytic, debridement, fibrinolytic or proteolytic enzymes, papain, papain-urea, and the like; antihistamines such as chlorcyclizine hydrochloride, diphenylhydramine hydrochloride, tripelennamine hydrochloride, and the like; antiepileptics such as nitrazepam, meprobamate, clonazepam, and the like; coronary vasodilators such as nitroglycerine, dipyridamole, erythritol, tetranitrate, pentaerythritol tetranitrate, propatyinitrate, and the like; dermatologicals such as retinal, retinol, retinoic acid and their derivatives, hydroxyacids, alphaketoacids, and the like; and other drugs such as benzoyl peroxide, podofilox, masoprocol, nicotine, scopolamine, nitroglycerine, fluorouracil, hydrocolloids, hydroquinone, monobenzone, tretinoin and acyclovir. Preferred drugs for use herein include acne-benzoyl peroxide, Vitamin C, and Vitamin E.

These and other drugs are provided in some suitable diffusable hydrophilic medium, e.g., an ointment, paste or other hydrophilic vehicle such as an emulsion formulation, in accordance with known established pharmaceutical formulating practice. Examples of emulsion formulations for use herein include the following:

1. Vegetable oil 10.0%, Petrolatum 3.0%, Beeswax, 12.0%, Cetearyl alcohol 4.0%, Light mineral oil 22.0%, Preservative 0.2%, Antioxidant 0.1%, Borax 0.7%, and Purified water qs to 100.0%;

2. Glyceryl monostearate 10.0%, Glycerin 12.0%, Ceryl trimethyl ammonium salt 0.1%, and Purified water qs to 100.0%;

3. Stearyl alcohol 23.0%, Petrolatum 23.0%, Hyamine 10×2.0%, Glycerin 10.0%, and Purified water qs to 100%;

4. Stearyl alcohol 25.0%, Petrolatum 25.0%, Propylene glycol 10.0%, Sodium lauryl sulfate 1.0, Methyl paraben 0.025%, Propyl paraben 0.015%, and Purified water qs to 100.0%;

5. Tween 85 10.0%, Arlacel 85 1.0%, Beeswax 2.0%, Lanolin 4.0%, Stearic acid 15.0%, Light mineral oil 23.0%, Preservative qs, Sorbitol 10.0%, and Purified water qs to 100.0%; and 6. Lanolin 28.0%, Beeswax 14.0%, Vegetable oil 20.0%, Light mineral oil 10.0%, Cholesterol 2.0%, Preservative qs, Antioxidant qs, Borax 0.8%, and Purified water qs to 100.0%. In those cases where rapid penetration of the drug is desired, it may be advantageous to include one or more penetration enhancers in the diffusable drug composition. Included among the penetration enhancers that can be used herein are butylene glycol, capric acid, caproic acid, caprylic acid, caprylic/capric triglyceride, diethylene glycol, diethylene glycol monoethyl ether, glycerin, glyceryl dioleate, glycerol monooleate, glycerol trioleate, hexylene glycol, isopropylmyristate, isopropylpalmitate, linoleic acid, methyl laurate, oleic acid, oleyl alcohol, polyethylene glycol 200, polyethylene glycol dilaurate, propyl oleate, propylene glycol, squalene, and the like.

The hydrophilic drug composition used herein can also contain at least one other pharmacologically active or nonactive substance, e.g., narcotic analgesics such as codeine, oxycodeine, dihydrocodeine, hydrocodone, levorphanol, morphine, and the like.

In general, drug reservoir 24 will possess a moisture vapor permeable, but hydrophilic drug composition impermeable, barrier layer 15. As one skilled in the art can readily appreciate, barrier layer 15 can be applied to one side of reservoir 24 either prior to, during or following barrier layer 15 being applied to adhesive layer 14 employing any suitable technique known to one skilled in the art, e.g., by way of an adhesive, or by coating a molten material on one side of drug reservoir 24 or adhesive layer 14 or by coating a solution containing a solvent on one side of reservoir 24 or adhesive layer 14 wherein the solvent will substantially evaporate thereby forming a thin film, i.e., barrier layer 15. Thus, barrier layer 15 separates drug reservoir 24 from adhesive layer 14. The barrier layer 15 therefore prevents or inhibits any significant migration of the hydrophilic drug composition from drug reservoir 24 into adhesive layer 14 once the drug composition has been incorporated into reservoir 24 where it could destroy or impair the effectiveness of adhesive layer 14 in securing the drug delivery device to the skin. Another advantageous characteristic of the drug delivery device herein is its ability to maintain continuous contact between the hydrophilic drug composition and the skin thus assuring that the drug will be constantly available at the site of its administration. Useful materials for forming hydrophilic drug composition barrier layer 15 include, for example, perforated polyethylene, perforated polyurethane and the like. The thickness of the barrier layer 15 can vary from less than about 2.0 mils and preferably less than about 1.0 mils.

Drug delivery device 10 can be manufactured in a variety of sizes and shapes and can be planar or three-dimensional.

Figure 2A:
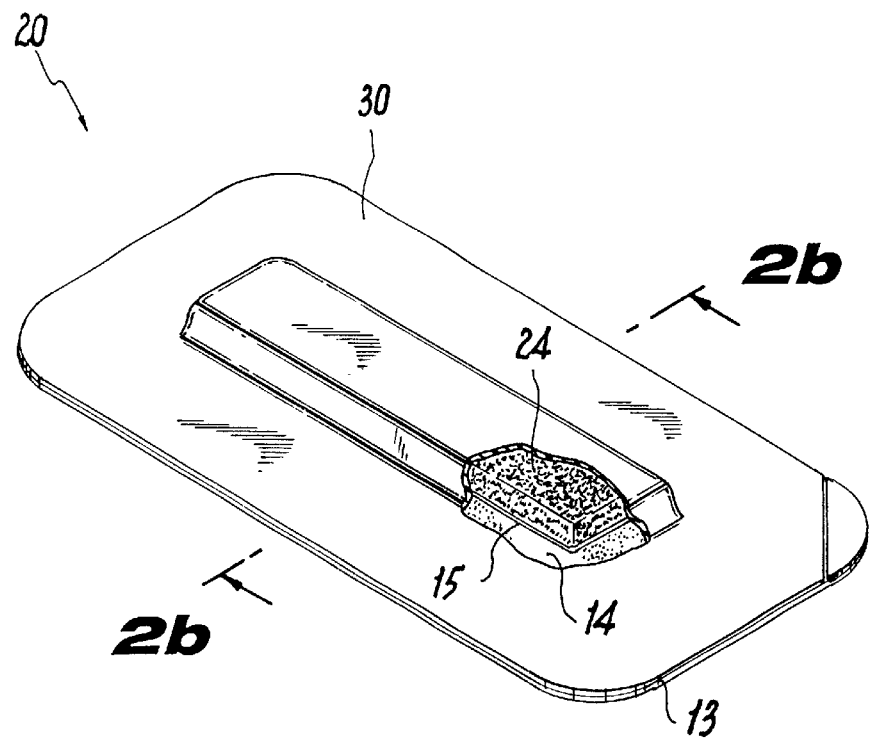
Figure 2B:
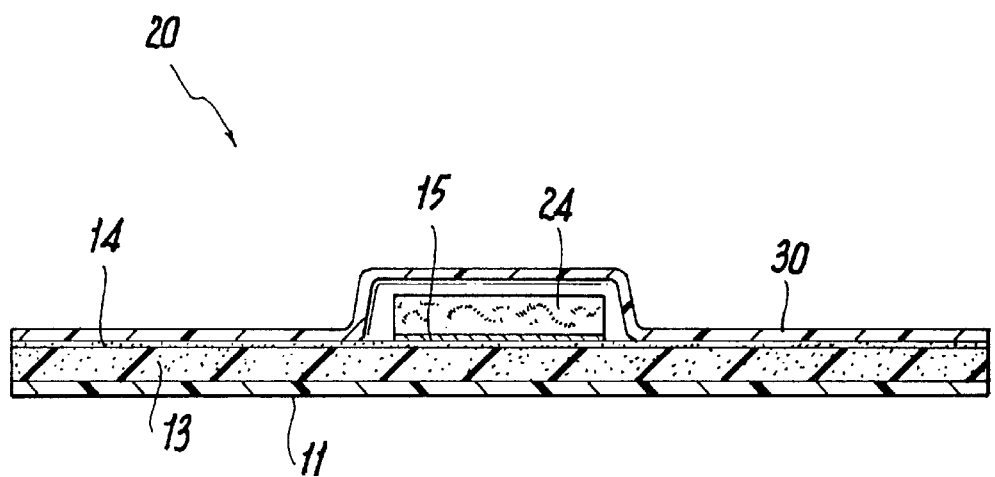

The drug delivery device can also possess a protective cover 30 instead of release liners 17a and 17b as shown generally in FIG. 2a at 20. Covers of this kind are known from U.S. Pat. No. 4,627,429, the contents of which are incorporated by reference herein. In general, protective cover 30 can be made, for example, of a heat-sealable aluminum foil film laminate with heat-sealable surface down. A formed cup, dome or square in cover 30 allows room for reservoir 24 with the other portion of cover 30 being placed over the adhesive layer 14 as generally depicted in FIG. 2b.

What is claimed is:

1. A drug delivery device which comprises:
   a) a moisture vapor permeable, liquid impermeable flexible thermoplastic backing layer possessing upper and lower surfaces;
   b) a moisture vapor permeable, flexible, oleophilic thermoplastic foam layer possessing upper and lower surfaces, the upper surface of the foam layer being nonadhesively bonded to, and substantially coextensive with, the lower surface of the backing layer;
   c) a pressure sensitive adhesive layer possessing a lower surface presenting a skin-contacting region and an upper surface adherent to, and substantially coextensive with, the lower surface of the foam layer; and,
   d) a drug reservoir possessing a lower drug-releasing surface and an upper drug barrier surface, the reservoir containing a medicinally effective amount of at least one hydrophilic drug composition, the drug reservoir further possessing a moisture vapor permeable, but hydrophilic drug composition impermeable, barrier layer having an upper and lower surface, its lower surface in adherent contact with the drug barrier surface of the drug reservoir and its upper surface contacting a portion of the lower surface of the pressure sensitive adhesive layer, wherein the barrier layer prevents any significant migration of the drug composition from the drug reservoir into the skin-contacting region of the lower surface of the pressure sensitive adhesive layer wherein the drug delivery device remains adhered to, and the drug-releasing surface of the drug reservoir remains in contact with, skin upon application of the drug delivery device thereto.

2. The drug delivery device of claim 1 wherein the foam layer and the thermoplastic backing layer are each fabricated from a polyurethane resin.

3. The drug delivery device of claim 1 wherein the moisture vapor transmission rate is at least about 1000 g/m$^2$/24 h at 100% relative humidity and 32° C.

4. The drug delivery device of claim 1 wherein the bond strength between the thermoplastic backing layer and the foam layer is at least about 2 N.

5. The drug delivery device of claim 1 wherein the bond strength between the thermoplastic backing layer and the foam layer is at least about 3 N.

6. The drug delivery device of claim 4 wherein the peel strength of the device is at least about 20 percent less than the bond strength between the thermoplastic backing layer and the foam layer.

7. The drug delivery device of claim 4 wherein the peel strength of the device is at least about 40 percent less than the bond strength between the thermoplastic backing layer and the foam layer.

8. The drug delivery device of claim 5 wherein the peel strength of the device is at least about 20 percent less than the bond strength between the thermoplastic backing layer and the foam layer.

9. The drug delivery device of claim 5 wherein the peel strength of the device is at least about 40 percent less than the bond strength between the thermoplastic backing layer and the foam layer.

10. The drug delivery device of claim 5 wherein the thermoplastic backing layer is flame laminated or vacuum laminated to the foam layer.

11. The drug delivery device of claim 1 wherein the drug reservoir is fabricated from a material selected from the group consisting of polyurethane foam, woven cellulose and nonwoven cellulose.

12. The drug delivery device of claim 1 wherein the hydrophilic drug composition barrier layer is fabricated from a material selected from the group consisting of perforated polyethylene and perforated polyurethane.

13. The drug delivery device of claim 1 wherein the thickness of the hydrophilic drug composition barrier layer is less than 0.001 inches.

14. The drug delivery device of claim 1 wherein the hydrophilic drug comprises a polar material and a topical analgesic selected from the group consisting of menthol, methyl salicylate, camphor, capsaicin and their mixtures.

15. The drug delivery device of claim 14 wherein the polar material is selected from the group consisting of water and alcohol.

16. The drug delivery device of claim 1 wherein the hydrophilic drug comprises a polar material and hydrocortisone.

17. The drug delivery device of claim 16 wherein the polar material is selected from the group consisting of water and alcohol.

18. The drug delivery device of claim 1 wherein the hydrophilic drug composition comprises a drug and at least one polar material.

19. The drug delivery device of claim 18 wherein the polar material is selected from the group consisting of water and alcohol.

20. The drug delivery device of claim 18 wherein the active or non-active component is a narcotic analgesic.

21. The drug delivery device of claim 20 wherein the narcotic analgesic is selected from the group consisting of codeine, oxycodeine, dihydrocodeine, hydrocodeine, levorphanol and morphine.

22. The drug delivery device of claim 1 further comprising a cover covering the adhesive layer and drug reservoir and being bonded to the adhesive layer.

* * * * *